United States Patent [19]
Davis

[11] Patent Number: 5,688,121
[45] Date of Patent: Nov. 18, 1997

[54] CORRUGATED SALIVA EJECTOR

[75] Inventor: Ralph L. Davis, Genoa City, Wis.

[73] Assignee: Filtertek Inc., Hebron, Ill.

[21] Appl. No.: 547,028

[22] Filed: Oct. 23, 1995

[51] Int. Cl.$^6$ .................................................. A61C 17/06
[52] U.S. Cl. ........................................ 433/96; 433/91
[58] Field of Search ............................ 433/91, 94, 95, 433/96; 604/281, 282, 902

[56] References Cited

U.S. PATENT DOCUMENTS

| | | |
|---|---|---|
| 128,257 | 6/1872 | Snyder. |
| 1,192,408 | 7/1916 | Frame. |
| 3,409,224 | 11/1968 | Harp et al.. |
| 3,476,144 | 11/1969 | Krantz. |
| 3,631,654 | 1/1972 | Riely. |
| 3,890,712 | 6/1975 | Lopez. |
| 4,051,981 | 10/1977 | Mandlak .................... 222/189 |
| 4,158,916 | 6/1979 | Adler. |
| 4,265,621 | 5/1981 | McVey ........................ 433/91 |
| 4,287,065 | 9/1981 | Raines ....................... 210/445 |
| 4,417,874 | 11/1983 | Andersson et al. ........... 433/96 |
| 4,587,687 | 5/1986 | Ikonen et al. ............... 15/314 |
| 4,690,757 | 9/1987 | Mathus et al. .............. 210/232 |
| 4,852,564 | 8/1989 | Sheridan et al. ............ 604/281 |
| 4,900,441 | 2/1990 | Graus et al. ................ 210/446 |
| 5,076,787 | 12/1991 | Overmyer ................... 433/95 |
| 5,078,603 | 1/1992 | Cohen ........................ 433/91 |
| 5,204,004 | 4/1993 | Johnston et al. ............. 210/651 |
| 5,425,637 | 6/1995 | Whitehouse et al. ......... 433/96 |
| 5,476,630 | 12/1995 | Orsing ........................ 433/96 |
| 5,547,375 | 8/1996 | Schneider ................... 433/96 |

FOREIGN PATENT DOCUMENTS

| | | |
|---|---|---|
| 3316397.9 | 1/1985 | Germany. |
| WO 82/00764 | 3/1982 | WIPO. |
| WO 92/19437 | 11/1992 | WIPO. |

*Primary Examiner*—Cary E. O'Connor
*Attorney, Agent, or Firm*—Brinks Hofer Gilson & Lione

[57] ABSTRACT

A saliva ejector having a hollow tube including a cylindrical wall, a first end for placement within an oral cavity, and a second end for attachment to a suction hose. A flowpath is defined within the tube. The ejector includes a first corrugated portion defined in the cylindrical wall, a second corrugated portion defined in the cylindrical wall, and a filter element secured across the flowpath. The bending qualities of the first corrugated portion differ from the bending qualities of the second corrugated portion, thus allowing for a wide variety of bendable configurations.

12 Claims, 2 Drawing Sheets

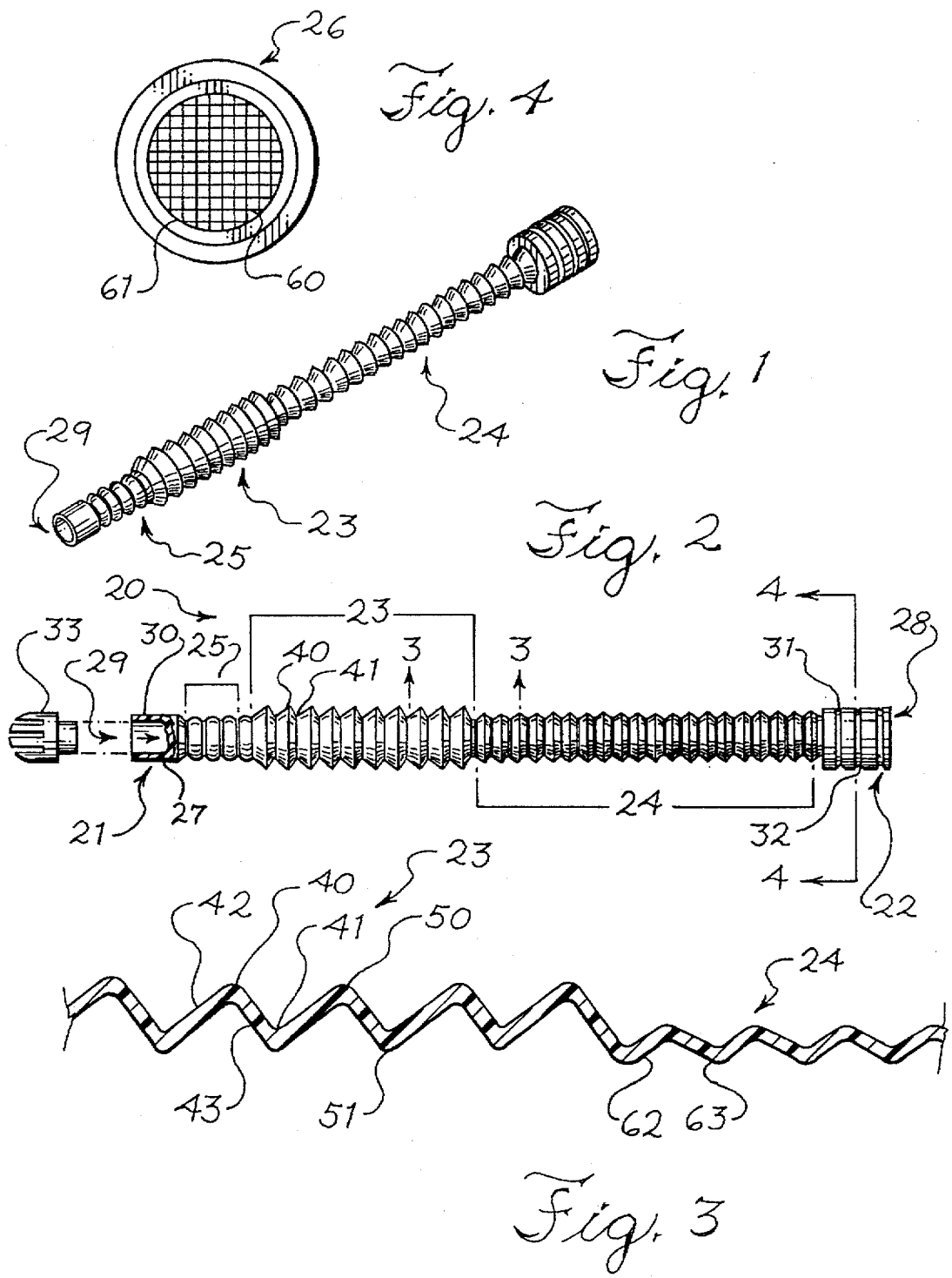

CORRUGATED SALIVA EJECTOR

BACKGROUND OF THE INVENTION

This invention relates to an improved saliva ejector. More particularly, the invention relates to an improved saliva ejector having a corrugated, bendable shape.

Perhaps the most widely used type of saliva ejector is in the configuration of a tubular extension of pliable, semi-rigid Polyvinyl Chloride ("PVC") material which internally incorporates a bendable metal wire into its sidewall for nearly its entire length. The metal wire provides for retention of the saliva ejector in a bent shape to comfortably fit the mouth of the patient during a particular dental procedure. One end of the ejector is attached to the hose of the suction system, and the other end of the ejector is typically capped with a screen or crown to reduce or prevent aspiration of delicate oral tissues.

These types of wire-embedded saliva ejectors have shortcomings, however. For example, the embedded bendable wire may deform the cylindrical wall of the plastic tube of the ejector, thereby causing the cross-section of the ejector to be somewhat oblong rather than circular. This irregular cross-section may prevent an adequate seal from forming between the end of the saliva ejector and the end of the suction hose, thereby reducing the amount of suction that can be used within the oral cavity. Furthermore, the wire-embedded saliva ejectors are relatively heavy, and may become uncomfortable within a patient's mouth after a long period of time. Also, the bendable wire and the thick tubing of the saliva ejector may prevent a more angled bending of the ejector, because a severe angle may close off the tube and decrease or eliminate the suction through the ejector.

Another problem associated with previous saliva ejector designs relates to the buildup of amalgam within dental aspirator systems. In particular, certain saliva ejector designs allowed the amalgam particles retrieved from a patient's mouth to pass through to the central aspirator system and accumulate within it. Dental aspirators typically utilize an amalgam separator located near the centralized vacuum source of the system. If the system is not cleaned frequently, the buildup of amalgam in the separator can result in bacterial contamination of the suction lines in addition to the water waste lines output from the suction system. This contamination may travel through the suction lines and subsequently reach the patient. This is unacceptable in the sterile environment dentistry demands.

Therefore, there is a need for an inexpensive, light weight, and easily formable saliva ejector for use with dental aspirator systems.

Furthermore, there is a need for an inexpensive, sanitary, and easily accessible filtering device for preventing excessive buildup of amalgam within the amalgam separator in a dental suction system.

SUMMARY OF THE INVENTION

The preferred embodiment of the invention disclosed herein provides a corrugated saliva ejector incorporating a removable filter for connection to a suction hose of a dental aspirator system.

In one aspect of the present invention, a saliva ejector is provided having a hollow tube including a cylindrical wall, a first end for placement within an oral cavity, and a second end for attachment to a suction hose. A flowpath is defined within the tube. The ejector also includes a first corrugated portion defined in the cylindrical wall, a second corrugated portion defined in the cylindrical wall, and a filter element secured across the flowpath. The bending qualities of the first corrugated portion differ from the bending qualities of the second corrugated portion.

In another aspect of the invention, the first corrugated portion and the second corrugated portion include a plurality of ridges each having a long side and a short side. The long side faa the first corrugated portion and the long side of the second corrugated portion are of different lengths, and the short side of the first corrugated portion and the short side of the second corrugated portion are also of different lengths.

In yet another aspect of the invention, a method of removing amalgam from an oral cavity includes the steps of providing a suction hose connected to a suction system, attaching one of the above-described saliva ejectors to the suction hose, and applying suction to the saliva ejector.

The saliva ejector overcomes problems with previous metal-wire encased saliva ejectors by utilizing multiple corrugated portions to allow bending and manipulation of the ejector. The multiple corrugated portions provide a wider range of configurations of the ejector to assist in various dental procedures, yet retain a degree of stiffness desirable for ease of use. Furthermore, the design allows for a lightweight, all-plastic design which simplifies production and cost.

These and other features and advantages of the invention will become apparent upon the review of the following detailed description of the presently preferred embodiments of the invention, taken in conjunction with the appended drawings.

BRIEF DESCRIPTION OF THE DRAWINGS

FIG. 1 is a perspective view of a first embodiment of the saliva ejector of the present invention.

FIG. 2 is a side view of the saliva ejector of FIG. 1.

FIG. 3 is a cross-sectional view taken along line 3—3 of FIG. 2.

FIG. 4 is a cross-sectional view taken along line 4—4 of FIG. 2.

DETAILED DESCRIPTION OF THE DRAWINGS AND PREFERRED EMBODIMENTS OF THE INVENTION

Figure 5:
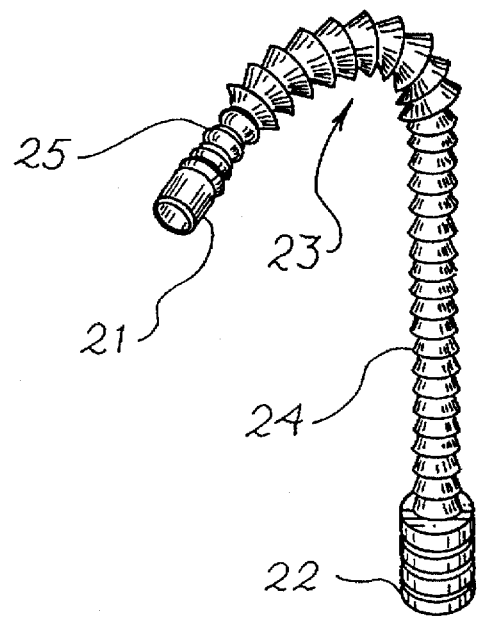
FIG. 5 is a perspective view of the saliva ejector of FIG. 1 showing the ejector bent at one of the corrugated portions.

A perspective view of a first preferred embodiment of the invention is shown in FIGS. 1 and 2. Preferably, tubular saliva ejector 20 includes a first end 21 and a second end 22, with multiple corrugated portions 23, 24, and 25 defined therebetween. The saliva ejector 20 is generally defined by a plastic wall 27 extruded into the form of a cylinder.

The saliva ejector 20 preferably defines an elongated flow path 30 between first end 21 and second end 28. The only openings into the flow path 30 are through opening 29 defined in the first end 21 of the saliva ejector 20, and opening 28 defined within the second end 22 of the saliva ejector 20. The multiple corrugated portions 23, 24, and 25 extend nearly the entire length of the ejector 20 between the first end 21 in the second end 22. Preferably, the corrugated portions 23, 24, and 25 are formed with bellows-like folds in the wall 27 to obtain ridges 40 and grooves 41 around the circumference of saliva ejector 20. The ridges 40 form outwardly extending peaks, while the grooves 41 are formed below and adjacent to the successive peaks. Each ridge 40 preferably includes individual sides having different transverse lengths, as can be seen in more detail in FIG. 3. The various lengths referred to herein refer to the transverse distances between the ridges and the grooves as illustrated in the cross-sectional view of FIG. 3, and do not refer to the circumferential lengths around the saliva ejector 20.

As shown in FIG. 3, ridge 40 is defined in wall 27 as having a long side 42 and a short side 43 between peaks 40 and 50. The ridges 40 and grooves 41 and 51 are formed in this fashion so that the short side 43 can snap in and be retained underneath the long side 42 when pressing together the corrugated portion 23 in portion 24. Long side 62 and short side 63 are also illustrated in corrugated portion 24 as shown. A similar bellows-like corrugation is shown in U.S. Pat. No. 3,409,224. This conventional corrugation structure allows the corrugated portion 23, 24, or 25 to have unique bending qualities, in that they may be bent using relatively little force into different angles and shapes without significant resistance, while the bent corrugated portion remains in the bent form after the force has been removed from the corrugated portion. Furthermore, the bending of the corrugated portions 23, 24, and 25 may be performed in a manner which results in a fairly sharp bending angle, such as an angle less than 90 degrees, without closing off the internal diameter of the flow path 30 significantly.

Figure 6:
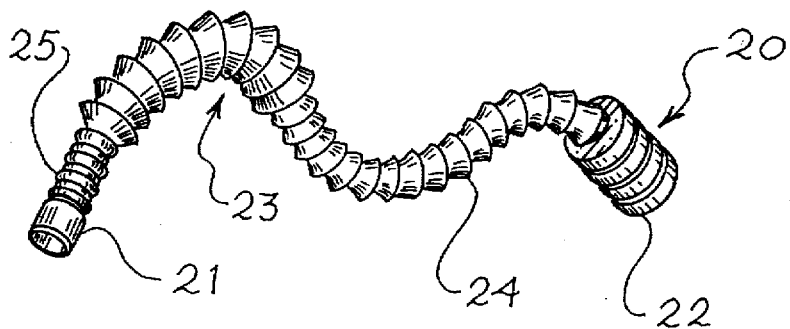
FIG. 6 is a perspective view of the saliva ejector of FIG. 1 bent at the corrugated sections into a configuration different from that of FIG. 4.

Preferably, corrugated portions 23, 24, and 25 will have ridges 40 and grooves 41 with longer sides 42 and 43 in wall 27 than will corrugated portions 24 and 25 and their sides 42 and 43. The resulting structure will allow corrugated portion 23 to have different bending qualities than corrugated portions 24 and 25, in that this area may be bent more sharply than the corrugated portions 24 and 25, as shown in FIGS. 5 and 6. Preferably, corrugated portions 24 and 25 will have the same corrugation dimensions of the long and short sides 62 and 63. This unique structure allows the saliva ejector to 20 to be bent into various configurations which are impossible to duplicate with a PVC saliva ejector having an enclosed metal wire.

In accordance with the present embodiment of the invention, a disc-shaped filter element may be fitted into second end 22. As shown in FIG. 4, filter element 26 includes a nylon mesh screen 60 encased in a plastic ring frame 61. The screen 26 captures any amalgam removed from the patient's mouth through opening 29 and flowpath 30 from entering the main suction and amalgam separator system. Furthermore, the removable filter element 26 simplifies the manufacture of the extruded saliva ejector 20, by allowing the filter element 26 to be snapped into the second end 22 after the extrusion of saliva ejector 20. Preferably, screen 60 is molded into the ring frame 61 via conventional injection molded methods.

Figure 7:
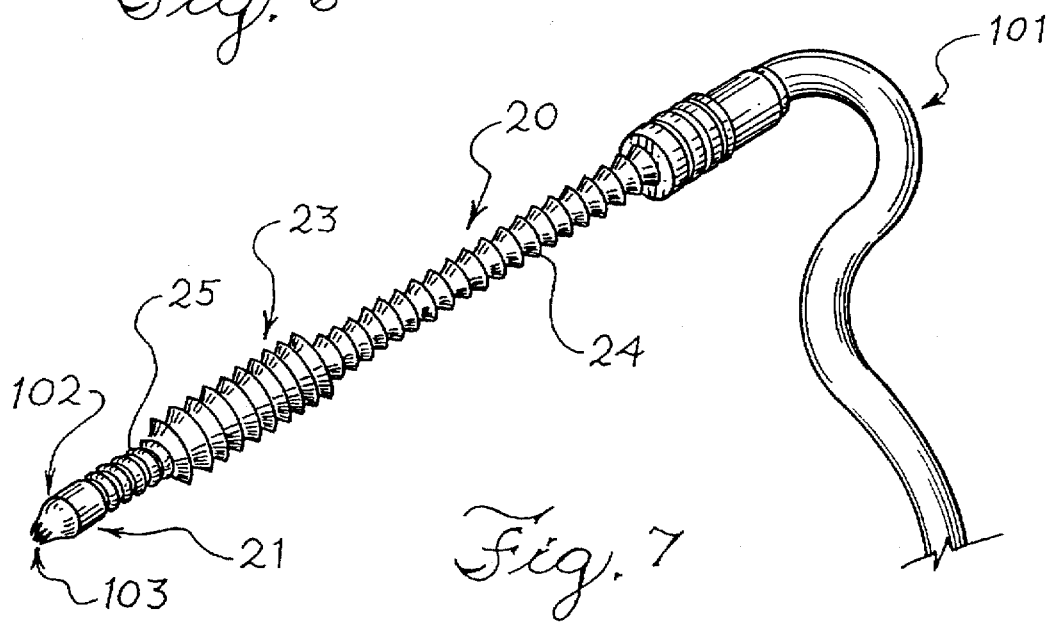
FIG. 7 is a perspective view showing the saliva ejector of FIG. 1 and its attachment to a suction hose of a dental aspirator system.

Second end 22 is slightly flared from the rest of saliva ejector 20 to allow attachment of the second end 22 to a suction hose 101 as shown in FIG. 7. The sizing of the flared second end 22 may be matched to fit suction hoses from various manufacturers. Preferably, the second end 22 has a plurality of outer grooves 31 and 32 defined around it in order to improve the frictional fit between the saliva ejector 20 and the suction hose 101. Furthermore, the grooves 31 and 32 increase the seal between the saliva ejector 20 and the suction hose 101.

The first end 21 of saliva ejector 20 preferably has a simple opening 29 of a diameter which may allow the receipt of a crown member 33, as shown in FIG. 3. The crown member 33 may be simply snapped or glued to the first end 21 of saliva ejector 20 after the saliva ejector 20 is extruded. The crown 33 prevents suction aspiration of the oral tissues of the patient. The crown 33 need not be used with the saliva ejector 20 if this kind of aspiration is not a problem.

In the alternative, the first end 21 may be crimped and cut as shown in the crimped portion 102 of FIG. 7 to provide protection against aspiration of oral tissues by the tip. The crimping may utilize heat sealing and cutting to provide a reduced-size opening 103 in the ejector, or multiple openings to protect against excessive suction. The crimping procedure provides a simpler method of manufacturing the ejector 20.

Of course, it should be understood that a wide range of changes and modifications can be made to the embodiments described above. For example, the filter element could have a shape other than planar and round. Also, the various multiple corrugation portions may be located in different areas of the saliva ejector than those shown. Furthermore, the lengths of the long and short sides may actually be the same within a particular corrugated portion. It is thus not necessary for a corrugated portion to have bending qualities that retain a saliva ejector configuration strictly in a configured shape.

It is therefore intended that the foregoing detailed description be regarded as illustrative rather than limiting and that it be understood that it is the following claims, including all equivalents, which are intended to define the scope of the invention.

I claim:

1. A saliva ejector comprising:
   a hollow tube having a cylindrical wall, a first end for placement within an oral cavity, and a second end for attachment to a suction hose, said tube defining a flowpath therethrough;
   a first corrugated portion defined in said cylindrical wall;
   a second corrugated portion defined in said cylindrical wall;
   a filter element secured across said flowpath;
   wherein the bending qualities of said first corrugated portion differ from the bending qualities of said second corrugated portion.

2. The saliva ejector of claim 1 wherein the only openings defined in said ejector consist of an opening defined in said first end and an opening defined in said second end.

3. The saliva ejector of claim 2 wherein said filter element comprises a flat screen.

4. The saliva ejector of claim 3 wherein said screen further comprises nylon.

5. The saliva ejector of claim 2 wherein said first corrugated portion and said second corrugated portion further comprise a plurality of ridges each having a long side and a short side.

6. A saliva ejector comprising:
   a hollow tube having a cylindrical wall, a first end for placement within an oral cavity, and a second end for attachment to a suction hose, said tube defining a flowpath therethrough;
   a first corrugated portion defined in said cylindrical wall, said first corrugated portion including a plurality of ridges each having a long side and a short side;
   a second corrugated portion defined in said cylindrical wall, said second corrugated portion including a plurality of ridges each having a long side and a short side;

a filter element secured across said flowpath; and wherein said long side of said first corrugated portion and said long side of said second corrugated portion are of different lengths, and said short side of said first corrugated portion and said short side of said second corrugated portion are of different lengths.

7. The saliva ejector of claim 6 wherein the only openings defined in said ejector consist of an opening defined in said first end and an opening defined in said second end.

8. The saliva ejector of claim 7 wherein said filter element comprises a flat screen.

9. The saliva ejector of claim 6 wherein the pliability of said first corrugated portion differs from the pliability of said second corrugated portion.

10. The saliva ejector of claim 6 wherein said tube further comprises extruded plastic.

11. The saliva ejector of claim 6 further comprising a crown secured to said first end.

12. A method of removing amalgam from an oral cavity, said method comprising:

providing a suction hose connected to a suction system;

attaching a saliva ejector to said suction hose, said saliva ejector including:

a tube defining a flowpath therethrough, a first corrugated portion defined in said cylindrical wall, a second corrugated portion defined in said cylindrical wall, a filter element secured across said flowpath, wherein the bending qualities of said first corrugated portion differ from the bending qualities of said second corrugated portion; and applying suction to said saliva ejector.

* * * * *